US012622633B2

(12) United States Patent
Kyriacou et al.

(10) Patent No.: US 12,622,633 B2
(45) Date of Patent: May 12, 2026

(54) SYSTEM FOR MONITORING ANASTOMOSES

(71) Applicant: City, University of London, London (GB)

(72) Inventors: Panicos Kyriacou, London (GB); Mohamed Thaha, London (GB); Karthik Budidha, London (GB)

(73) Assignee: City, University of London, London (GB)

( * ) Notice: Subject to any disclaimer, the term of this patent is extended or adjusted under 35 U.S.C. 154(b) by 838 days.

(21) Appl. No.: 17/637,620

(22) PCT Filed: Aug. 24, 2020

(86) PCT No.: PCT/EP2020/073604
§ 371 (c)(1),
(2) Date: Feb. 23, 2022

(87) PCT Pub. No.: WO2021/037782
PCT Pub. Date: Mar. 4, 2021

(65) Prior Publication Data
US 2022/0273229 A1 Sep. 1, 2022

(30) Foreign Application Priority Data

Aug. 23, 2019 (GB) ...................................... 1912161

(51) Int. Cl.
*A61B 5/00* (2006.01)
*A61B 5/026* (2006.01)
*A61B 5/1455* (2006.01)
*A61B 5/1459* (2006.01)

(52) U.S. Cl.
CPC .......... *A61B 5/4255* (2013.01); *A61B 5/0084* (2013.01); *A61B 5/0261* (2013.01); *A61B 5/14552* (2013.01); *A61B 5/1459* (2013.01); *A61B 2562/166* (2013.01)

(58) Field of Classification Search
CPC ... A61B 5/4255; A61B 5/0084; A61B 5/0261; A61B 5/14552; A61B 5/1459; A61B 2562/166; A61B 17/11; A61B 17/1114
See application file for complete search history.

(56) References Cited

U.S. PATENT DOCUMENTS 9,339,221 B1 * 5/2016 Heaton, II ............. A61B 5/742
2014/0058234 A1 * 2/2014 Su ...................... A61B 5/14542
600/339
2018/0235484 A1 * 8/2018 Mozdzierz ............. A61B 17/29

* cited by examiner

*Primary Examiner* — Abid A Mustansir
(74) *Attorney, Agent, or Firm* — Secant IP, PLLC

(57) ABSTRACT

A system for monitoring anastomoses is provided. The system includes a probe and a control module in connection with the probe.
The probe includes optical sensor assemblies. Each sensor assembly includes an optical emitter and an optical detector The sensor assemblies are spaced from one another so that following insertion of the probe into a lumen of a subject, the sensor assemblies can interrogate limbs of an anastomosis. The control module is configured to operate the optical emitters to illuminate respective limbs of the anastomosis and to receive signals from the optical detectors, the signals being representative of light reflected by tissue of the limbs. The control module is also configured to compare signals from the detectors and derive therefrom an indication of tissue vitality in the lumen of either side of the anastomosis.

16 Claims, 3 Drawing Sheets

SYSTEM FOR MONITORING ANASTOMOSES

CROSS-REFERENCE TO RELATED APPLICATIONS

This application claims priority under 35 U.S.C. § 371 as a national stage application of PCT Application No. PCT/EP2020/073604, filed Aug. 24, 2020, which claims priority to GB 1912161.5, filed Aug. 23, 2019, each of which is hereby incorporated herein by reference in its entirety.

FIELD

This disclosure relates to a system for monitoring anastomoses, particularly but not exclusively to a system for monitoring intestinal anastomoses. An intraluminal probe and a control module for such systems are also disclosed.

In the following disclosure reference is made to intestinal and, in particular, colorectal anastomoses; but it will be appreciated that the system and components disclosed herein may be used in a variety of other applications and hence the scope of the present disclosure should not be construed as being limited only to the particular applications described herein.

BACKGROUND

Intestinal resection is a common surgical procedure in both elective and emergency settings. For colorectal cancer (CRC), the third most common malignancy with some 40,000 new cases per annum in the United Kingdom, it can be the only curative treatment.

Intestinal resections are also carried out for a variety of non-cancer conditions including inflammatory bowel disease (Crohn's disease, ulcerative colitis), diverticular disease, ischaemia of bowel, and traumatic bowel injuries.

From a patient's perspective, regaining continuity of the bowel after intestinal resection and being able to empty their bowel contents through their natural back passage is of paramount importance. Failure to achieve this can result in a loss of dignity and a reduced quality of life.

After intestinal resection, surgeons restore the continuity of the bowel by creating an intestinal anastomosis where the two cut ends of the intestine are joined together, typically with sutures or by using a stapling device. In recent times, as technology advances and instrumentation improves, an increasing number of restorative intestinal surgeries are tending to be carried out. Currently, a primary anastomosis tends to be considered to be the gold standard even in very low rectal cancers.

However, in a significantly high number of cases, an intestinal anastomosis cannot be performed and these patients are left with either a temporary or a permanent stoma. This is mainly due to concerns about adequate disease clearance (particularly for patients with low rectal cancers), concerns about the safe healing of an anastomosis, or to an anastomotic leak. The latter two primarily occur due to lack of sufficient blood supply to the site of the anastomosis.

For the normal healing process of an anastomosis to take place, it must have ample tissue perfusion to deliver the influx of inflammatory cells, growth factors, and oxygen. Insufficient microcirculation can lead to ischaemia which when prolonged can result in tissue necrosis, and subsequently an anastomotic leak. Anastomotic leaks cause spillage of intestinal contents leading to severe sepsis, multiorgan dysfunction and death in up to 32% of patients especially when the diagnosis and subsequent intervention is delayed. The incidence of an anastomotic leak following colonic resection is reported to be as high as 20%.

Successful management of the risk of an anastomotic leak requires early identification and early intervention prior to the establishment of systemic sepsis and organ failure. Often these patients require emergency re-laparotomy, take down of the failed anastomosis, clearance of the intra-abdominal/pelvic contamination and diversion of faecal stream by creation of a stoma, either an ileostomy or a colostomy. In many instances, such stomas are never reversed leading to persistently poor quality of life. Left sided anastomosis, particularly low rectal anastomosis tends to be more prone to failure and is often protected with a de-functioning temporary ileostomy (in up to 73% of patients). Such patients require a second operation to reverse the ileostomy and the incidence of such stomas becoming permanent are as high as 25%. The presence of a stoma also exposes the patients to a higher risk of surgical site infections.

Ability to accurately and dynamically measure perfusion to the intestine would allow surgeons to create a greater number of healthy anastomosis; objectively predict their successful healing; reduce the need for defunctioning ileostomies; and pre-empt timely interventions on a failing anastomosis—thereby reducing the morbidity and mortality associated with anastomotic leaks. Despite this understanding, accurate monitoring of intestinal circulation in patients with a newly formed anastomosis continues to be a distant goal.

Current methods for intra-operative assessment of intestinal viability include visual confirmation of the normal appearance and colour of intestinal serosa, visible and palpable pulsations in the mesenteric arterial arcade, presence of intestinal peristalsis and active bleeding from the cut edges of the intestine. These tests have a low sensitivity and a specificity, and are prone for inter-observer variability. Techniques such as Doppler Ultrasound, fluorescence and infrared imaging, and gastro-intestinal luminal $pCO_2$ have been used to assist surgical decision-making but have tended to be sub-optimal, and as a consequence have tended not be adopted as part of routine clinical procedures for similar reasons.

More recently it has been proposed to use indocyanine green (ICG) based immunofluorescence technology to confirm intestinal viability during construction of intestinal anastomosis, and this has been shown to be beneficial when compared to conventional observational methods. However, commercially available fluorescence imaging systems such as the so-called "PINPOINT" endoscope from Novadaq Technologies Inc. are extremely expensive. The cost per case of this device tends to be in the region of US$1,000, while the device itself costs more than US$200,000. It is also the case that this device is not suitable for dynamic monitoring of the intestinal blood supply during the postoperative period.

Thus, in the absence of a clinical tool to continually measure intestinal viability, postoperative monitoring of anastomosis depends on indirect parameters derived from clinical examinations including of vital signs (heart rate, blood pressure) and a series of blood tests. However, a specific and sensitive blood marker for early detection of intestinal ischaemia is not available. The diagnostic triad of leukocytosis, acid-base deficit and elevated serum phosphate concentration has been proposed as a distinctive characteristic of intestinal infarction. However, these changes often occur late, and tend to be non-specific. An increase in serum lactate, metabolic acidosis and left shift in the ratio of immature to mature neutrophils can also be used as markers for intestinal tissue damage. However, it is disadvantageous to have to wait for evidence of increasing serum lactate levels to proceed with further testing; in fact, intervention would tend to occur in patients with acute mesenteric ischaemia before lactic acidosis even develops. Another disadvantage associated with blood markers is that they are time consuming (blood sampling and analysis in a laboratory is required) to consider, do not permit continuous monitoring, are inconvenient to the patient, and are labour intensive.

Aspects of the present invention have been devised with the foregoing in mind.

SUMMARY

In accordance with a presently preferred embodiment of the present invention, there is provided a system for monitoring anastomoses, the system comprising a probe for interluminal insertion into a subject and a control module connectable to said probe, wherein: the probe comprises first and second optical sensor assemblies, each sensor assembly comprising an optical emitter operable to emit light and an optical detector for detecting light emitted by said optical emitter, said sensor assemblies being spaced from one another so that following insertion of said probe into a lumen of said subject said first sensor assembly can be utilised to interrogate one limb of an anastomosis and said second sensor assembly can be utilised to interrogate the other limb of said anastomosis; and the control module is configured to be capable of operating said optical emitters of said sensor assemblies for the illumination of respective limbs of said anastomosis and to be capable of receiving signals from the optical detectors of said optical sensor assemblies, said signals being representative of light reflected by tissue of the respective limbs of said anastomosis, said control module being further configured to compare signals from respective detectors of said sensor assemblies and derive therefrom an indication of tissue vitality in the lumen either side of said anastomosis.

The system disclosed is reliable, simple to use, reproducible, cost-effective and can improve a surgeon's ability to assess the adequacy of luminal (e.g. intestinal) perfusion during surgery. The system can also be employed to dynamically monitor tissue vitality, for example intestinal perfusion, across the limbs of the anastomosis post-operatively thereby providing distinct advantages to intermittent blood marker based monitoring.

In an implementation, said optical emitters of said respective sensor assemblies may be substantially identical. The optical detectors of said respective sensors assemblies may, preferably also may, be substantially identical. This arrangement provides for readily comparable signals from said detectors of said sensor assemblies. "Substantially identical", as will immediately be appreciated by persons of ordinary skill in the art, should not be taken to mean that the emitters (for example) have to emit light of precisely identical wavelengths, rather it should be taken to mean as similar to one another as is required to enable a signal from one detector to be reliably compared to the signal from the other.

In an envisaged implementation there is also provided a probe for the system disclosed herein, the probe comprising first and second optical sensor assemblies, each sensor assembly comprising an optical emitter operable to emit light and an optical detector for detecting light emitted by said optical emitter, said sensor assemblies being spaced from one another so that following insertion of said probe into a lumen of said subject said first sensor assembly can be utilised to interrogate one limb of an anastomosis and said second sensor assembly can be utilised to interrogate the other limb of said anastomosis. Such a probe can reliably and relatively inexpensively be fabricated.

The first and second optical assemblies may be coupled to a common elongate support, said first optical assembly being coupled to said support in the vicinity of a first end of the support, and said second optical assembly being coupled to said support in the vicinity of a second end of the support. The elongate support may comprise a planar body having opposing first and second faces, said first and second optical assemblies being coupled to said first face. The support may comprise a printed circuit board having circuity for electrically coupling said first and second sensor assemblies to said control module.

In one arrangement, the optical sensor assemblies may each comprise a plurality of optical emitters, the emitters of said plurality being configured to emit light at different wavelengths to one another. Optionally, the detectors of said optical sensor assemblies may be configured to be capable of detecting light having the wavelengths of said plurality of emitters.

In an envisaged arrangement, the support is sized for insertion into a catheter that can be inserted into said lumen.

Optionally, the probe can be decoupled from said control module for disposal.

Another aspect of the present disclosure pertains to a control module for the system disclosed herein, the control module comprising means capable of operating said optical emitters of said sensor assemblies for the illumination of respective limbs of said anastomosis and means capable of receiving signals from the optical detectors of said optical sensor assemblies, said signals being representative of light reflected by tissue of the respective limbs of said anastomosis, said control module further comprising means operable to compare signals from respective detectors of said sensor assemblies and derive therefrom an indication of tissue vitality in the lumen either side of said anastomosis.

The comparing means may be configured to derive an indication of one or more of tissue perfusion, blood flow, blood oxygenation, perfusion index (PI), incoming blood perfusion (PI), oxygen delivery (SpO2 and HbO2), oxygen consumption (HHb), and total blood volumes (tHb).

The control module may comprise means operable to determine if derived tissue vitality proximally of said anastomosis should vary by a predetermined degree from derived tissue vitality distally of said anastomosis. The predetermined degree may be chosen to be a degree of tissue vitality change that could be indicative of a potential failure of said anastomosis.

In one implementation the module may comprise means operable to alert an operator of said system if derived tissue vitality proximally of said anastomosis should vary by said predetermined degree from derived tissue vitality distally of said anastomosis. The control module may comprise a display and a display controller, said display controller being operable to control said display to display the indicator of tissue vitality derived by said comparing means distally of said anastomosis. The control module optionally be configured so that said display controller is operable to control said display to display the indicator of tissue vitality derived by said comparing means proximally of said anastomosis. The control module may comprise a display and a display controller, said display controller being operable to control said display to display an indication of tissue vitality difference between the tissue vitality indicator derived by said comparing means proximally of said anastomosis and the tissue vitality indicator derived by said comparing means distally of said anastomosis.

Other features, advantages and implementations of the present invention will be apparent from the following detailed description.

BRIEF DESCRIPTION OF THE DRAWINGS

Various aspects of the teachings of the present invention, and arrangements embodying those teachings, will hereafter be described by way of illustrative example with reference to the accompanying drawings, in which.

DETAILED DESCRIPTION

Figures 1, 2:
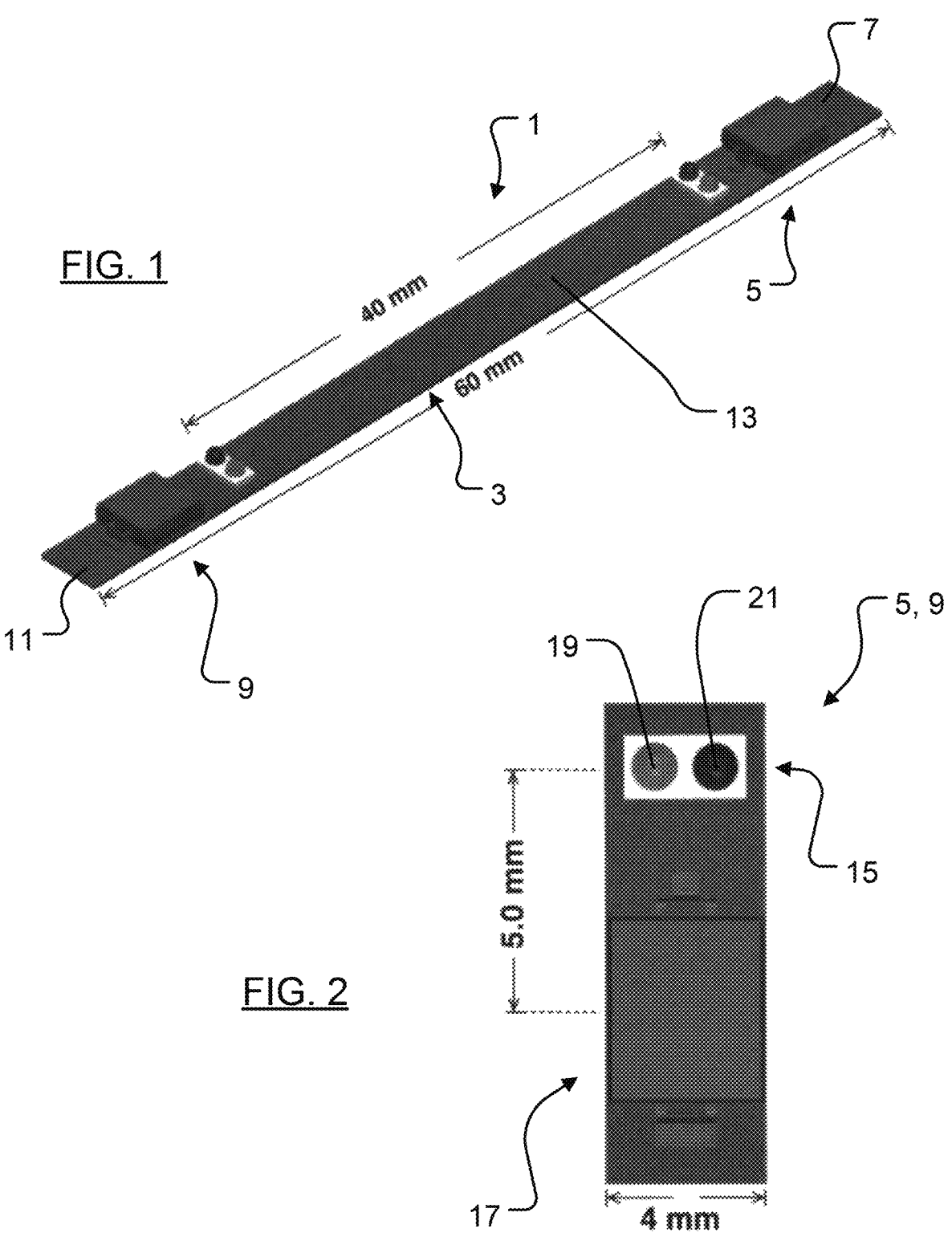
FIG. 1 is a schematic perspective view of a probe.
FIG. 2 is a schematic enlarged view of a region of the probe depicted in FIG. 1.

FIG. 1 is a schematic perspective view of a probe 1 for use with the system disclosed herein. The probe comprises a support 3 that is elongate and, in this implementation, substantially planar. A first optical sensor assembly 5 is coupled to the support 3 in the vicinity of a first end 7 of the support 3, and a second optical sensor assembly 9 is a coupled to the support 3 in the vicinity of a second end 11 of the support 3. In this instance the sensor assemblies 5, 9 are coupled to the same face 13 of the support 3. It will be apparent that they need not be, but such an arrangement is preferred as it reduces the height of the probe (as compared with a probe where the sensor assemblies are coupled to opposing faces of the support).

The sensor assemblies 5, 9 are spaced from one another along the support so that, once inserted into the lumen of the subject, an anastomosis can lie between the sensor assemblies 5, 9 thereby enabling the sensor assemblies 5, 9 to interrogate both limbs of the lumen. In the particular arrangement illustrated in FIG. 1, the sensor assemblies 5, 9 are spaced from one another by approximately 40 mm and the support is approximately 60 mm in length. It will be apparent, however, that the size of the probe may be varied as desired.

Referring now to FIG. 2, each sensor assembly (only one of which is depicted in FIG. 2) 5, 9 comprises an optical emitter 15 and an optical detector 17. In the particular example illustrated, the optical emitter 15 comprises two optical sources, which may comprise light emitting diodes. A greater or smaller number of sources may be provided, depending on which variables the probe is intended to investigate.

In this example, the emitter 15 includes a first source 19 that is operable to emit red light (for example, light having a wavelength of approximately 660 nm), and a second source 21 that is operable to emit infrared light (for example, light having a wavelength of approximately 940 nm). Light from the sources, which may be illuminated simultaneously or cyclically one after the other, travels from the probe into the tissue of the lumen where it is reflected and detected by the optical detector, which comprises in this particular example a photodiode having a radiant sensitive area of approximately 7 mm$^2$.

Figures 3, 4:
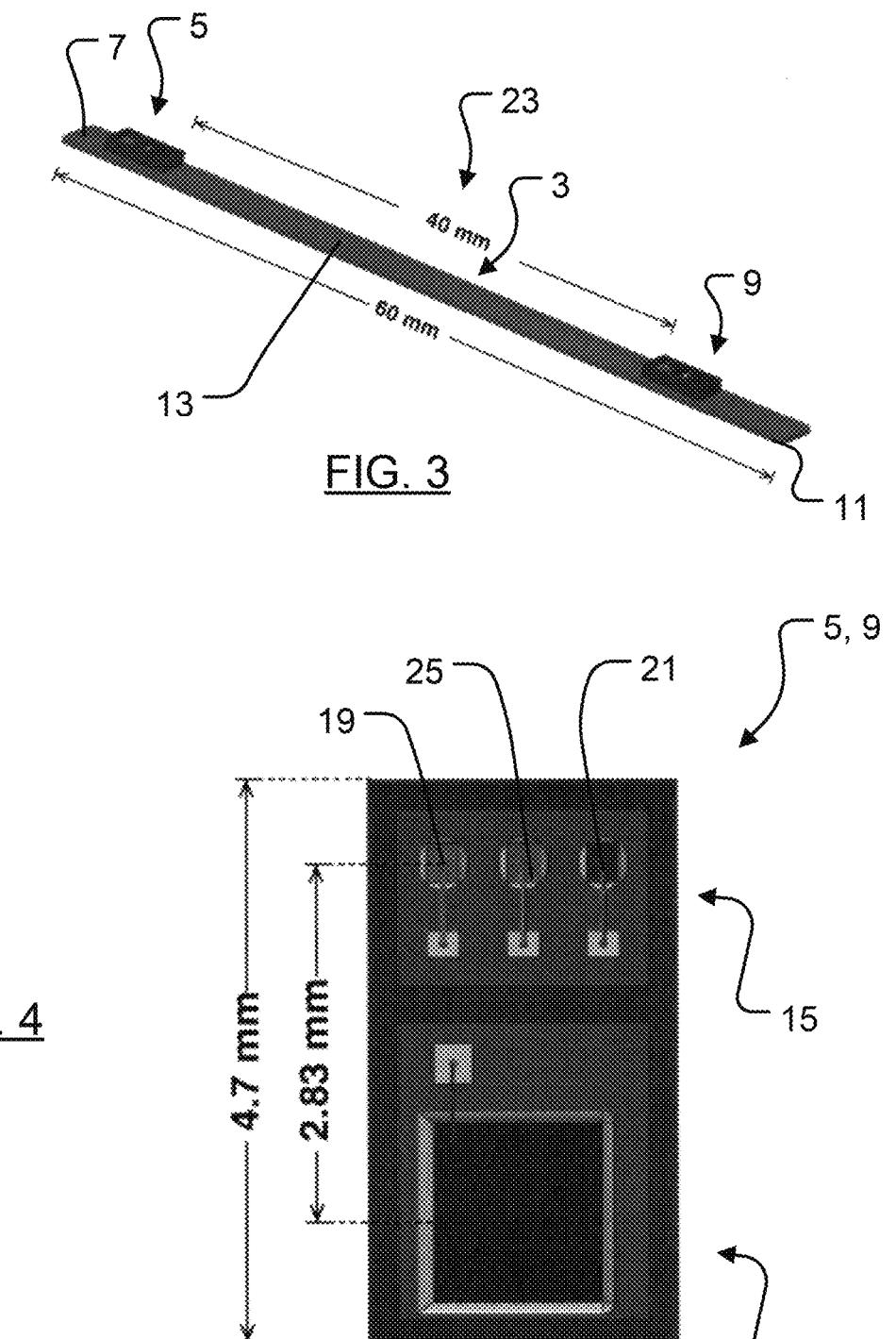
FIG. 3 is a schematic perspective view of another probe.
FIG. 4 is a schematic enlarged view of a region of the probe depicted in FIG. 3.

FIG. 3 is a schematic representation of another probe 23, and FIG. 4 is an enlarged view of a region of the probe depicted in FIG. 3. To avoid repetition, features of the probe 23 common to those of the probe 1 depicted in FIG. 1 have been given the same reference numerals and will not be described in detail.

The principal difference between the probe 23 of FIG. 3 and the probe 1 of FIG. 1 is that the sensor assemblies each include a third optical source 25 (for example, a light emitting diode) that is configured to emit green light (for example, light having a wavelength of approximately 525 nm). The addition of the green light source enhances the photoplethysmography (PPG) analysis that is enabled by the probe of FIG. 1 to enable multi-parametric PPG and multicomponent systems analysis like Near infrared spectroscopy (NIRS).

The sensor assembly of FIG. 4 is also significantly narrower than that of the sensor assembly of FIG. 2, and in this instance the optical detector 17 has a radiant sensitive area of approximately 1.7 mm$^2$. As will be appreciated, reducing the size of the probe increases the number of lumens into which the probe could be inserted.

Figure 5:
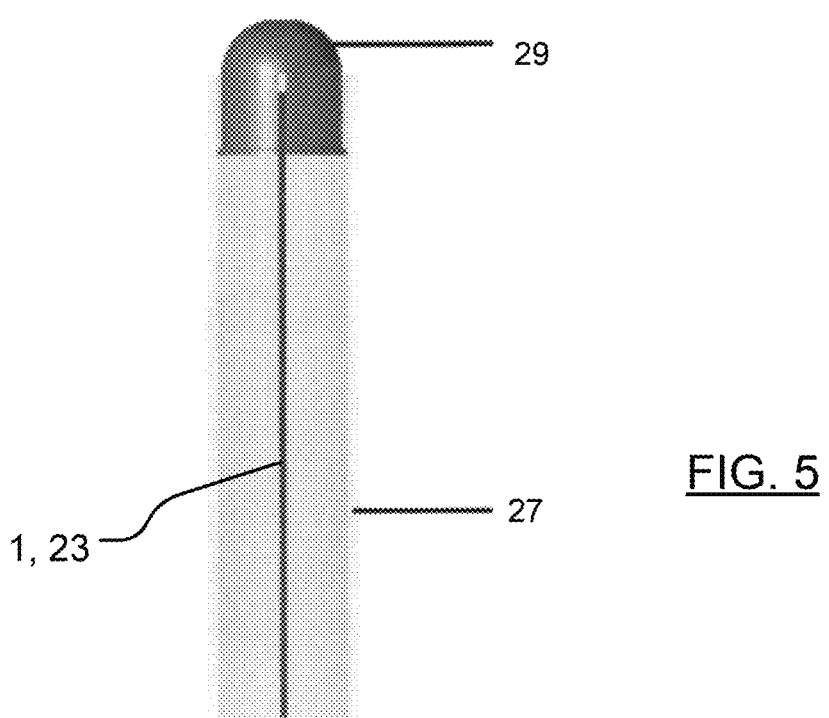
FIG. 5 is a schematic view of a probe inserted into a catheter.

Referring now to FIG. 5, in an envisaged implementation, the probe 1, 23 can be inserted into a catheter 27, for example an anal catheter, for insertion into a subject's lumen. In the arrangement shown in FIG. 5, the probe is retained in place by means of a slotted plug 29 that has a rounded outer surface and is push fitted into the end of the catheter. Appropriate electrical wiring, not shown, for connecting the probe to the control module can run inside of the catheter and out of the subject, where they can be connected to the control module. As an alternative to a wired probe, it is envisaged that the support may carry a wireless interface and a power source, so that the probe can be wirelessly interrogated by the control module.

Figure 6:
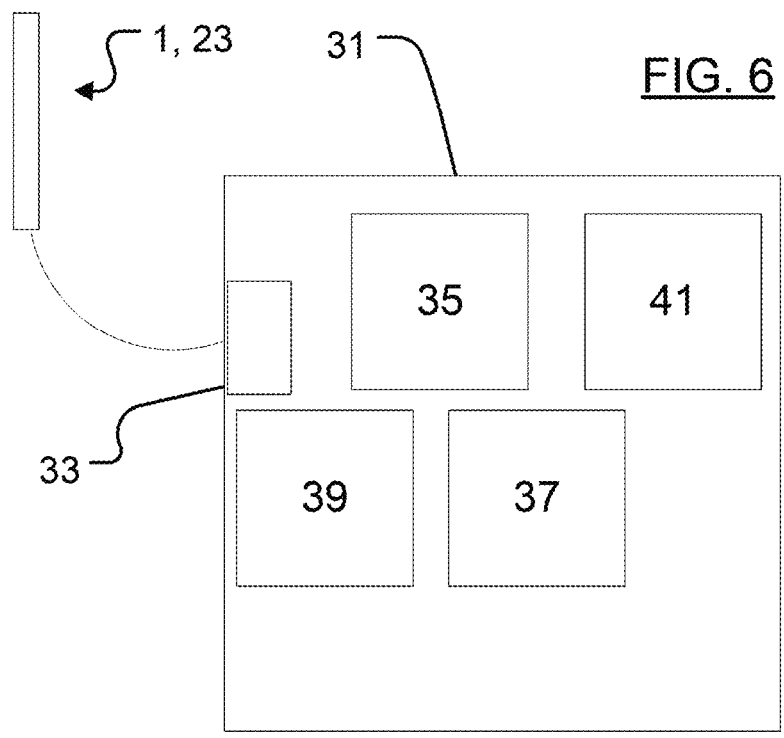
FIG. 6 is a diagrammatic representation of a system comprising a control module and a probe of the type depicted in any of FIGS. 1 to 4.

Referring now to FIG. 6, the probe 1, 23 is capable of being used with a control module 31 (typically a series of electronic components) to provide a system for monitoring anastomoses. The control module 31 includes an interface 33 for receiving electrical signals from the optical detectors 17 of the first and second optical sensor assemblies of the probe 1, 23, and for sending signals to the optical emitters 15 of the first and second sensor assemblies of the probe 1, 23 to turn the emitters on and off. A processor 35 is operable to compute, from the signals received at the control module 31 from the sensor assemblies an indication of tissue vitality in the tissue adjacent the first and second sensor assemblies. With the probe inserted into a lumen so that an anastomosis lies between the first and second sensor assemblies, a comparison module 37 can compare tissue vitality indicators proximally and distally of the anastomosis. By considering these indicators, an indication of the integrity of the anastomosis can be determined, and an alert module 39 may be configured to alert an operator of the system—for example by means of a display 41—if a potential failure of the anastomosis is envisaged.

It is apparent from the foregoing that an intra-luminal probe provides access to the mucosa of the anastomotic limbs facilitates minimally invasive continued monitoring of bowel perfusion especially in the post-operative period. In addition, the probe disclosed provides for estimation of additional perfusion parameters along with the PPG volumetric changes in order to provide the protection for a comprehensive assessment of the viability of the anastomosis. By means of the arrangement disclosed herein it is now possible to measure relative changes in concentrations of oxygenated (HbO2), reduced (HHb) and total haemoglobin (tHb), along with perfusion index (PI) and arterial oxygen saturation (SpO2). Thus, providing for continuous assessment of perfusion, oxygen delivery, oxygen consumption, total blood volumes, and blood flow at both ends of the anastomosis.

The minimally invasive indwelling optical probe disclosed herein utilises a multi-parametric approach to perform measurements of tissue perfusion and oxygenation from the intestinal mucosa, for example following colonic resection. The system enables the assessment of intestinal perfusion continuously from both ends of a newly formed anastomosis after resectional surgery, in one example by means of reflectance photoplethysmography and multicomponent systems analysis like Near infrared spectroscopy (NIRS).

The system disclosed enables the monitoring of relative changes in blood volume and tissue oxygenation from proximal and distal ends of an anastomosis, in one example using multi-wavelength reflection PPG and NIRS. As aforementioned, one implementation of the probe comprises two multi-wavelength sensor assemblies which shine near infrared and visible light into the intestinal mucosa and detect the changes in reflected and attenuated light. The light photons detected from the intestinal tissue are be converted into voltage signals containing a pulsatile component riding on top of a large quasi-static component. The pulsatile part of the signal represents the arterial blood, while the static component represents the light absorption of venous blood and the tissues. These signal components, acquired at different wavelengths, can then be used to estimate tissue vitality by means of any of a variety of physiological parameters such as oxygenated (HbO2), de-oxygenated (HHb) and total (tHb) haemoglobin concentrations, blood oxygenation (SpO2) and perfusion index (PI) by using advanced filtering techniques and signal-processing algorithms.

To achieve this, techniques such as multicomponent systems analysis (e.g. modified Beer-Lambert Law) have been applied for discerning the contribution of different haemoglobin species from the overall light absorption profile. However, the accurate quantification of changes in HbO2, HHb and tHb requires the knowledge of the optical path and penetration depth of light at the specified wavelengths in the intestinal tissue, which we have determined from Monte Carlo simulations of light photons diffusion through intestinal tissue to thereby enable the quantification of haemoglobin concentration changes. Furthermore, empirical calibration curves can be applied to the multi-wavelength signals for estimating the blood oxygenation similar to pulse oximetry. The morphological features of the signals can also be used to assess the adequacy of arterial perfusion by computing the perfusion index (PI). This multi-parametric analysis of PPG signals will provide a superior assessment of tissue vitality (for example intestinal perfusion) enabling the provision of a continuous estimation of incoming blood perfusion (PI), oxygen delivery (SpO2 and HbO2), oxygen consumption (HHb), and total blood volumes (tHb). Therefore, changes detected in these parameters can help the early identification of intestinal ischaemia and support clinicians in the early diagnosis of anastomotic failure.

It will be appreciated that whilst various aspects and embodiments of the present invention have heretofore been described, the scope of the present invention is not limited to the particular arrangements set out herein and instead extends to encompass all arrangements, and modifications and alterations thereto, which fall within the scope of the appended claims.

It should also be noted that whilst the accompanying claims set out particular combinations of features described herein, the scope of the present invention is not limited to the particular combinations hereafter claimed, but instead extends to encompass any combination of features herein disclosed.

The invention claimed is:

1. A system for monitoring anastomoses, the system comprising:

a probe for interluminal insertion into a subject; and a control module for connection to said probe, wherein:

the probe comprises first and second optical sensor assemblies, said first and second optical sensor assemblies each comprising an optical emitter operable to emit light and an optical detector for detecting light emitted by said optical emitter, said first and second sensor assemblies being spaced from one another so that following insertion of said probe into a lumen of said subject said first sensor assembly can be utilized to interrogate a first limb of an anastomosis and said second sensor assembly can be utilized to interrogate a second limb of said anastomosis, and the control module is configured to be capable of operating said optical emitters of said first and second optical sensor assemblies for to illuminate said first and second limbs of said anastomosis respectively, and to be capable of receiving signals from the optical detectors of said first and second optical sensor assemblies, signals from the optical detector of said first optical sensor assembly being representative of light reflected by tissue of said first limb of said anastomosis and signals from the optical detector of said second optical sensor assembly being representative of light reflected by tissue of said second limb of said anastomosis, said control module being further configured to compare the signals from the detectors of said first and second sensor assemblies with one another and derive therefrom an indication of tissue vitality in the lumen of either side of said anastomosis;

said control module being further configured to derive from the signals from the optical detectors of said first and second optical sensor assemblies an indication of tissue vitality selected from one or more of: tissue perfusion, blood flow, blood oxygenation, perfusion index (PI), incoming blood perfusion (PI), oxygen delivery (SpO2 and HbO2), oxygen consumption (HHb), and total blood volumes (tHb); and to determine if the indication of derived tissue vitality proximally of said anastomosis should vary by a predetermined degree from the indication of derived tissue vitality distally of said anastomosis.

2. The system according to claim 1, wherein the optical emitters of said first and second sensor assemblies are substantially identical.

3. The system according to claim 1, wherein said first and second optical assemblies are coupled to a common elongate support, said first optical assembly being coupled to said support near a first end of the support, and said second optical assembly being coupled to said support near a second end of the support.

4. The system according to claim 3, wherein said elongate support comprises a planar body having opposing first and second faces, said first and second optical assemblies being coupled to said first face.

5. The system according to claim 4, wherein said elongate support comprises a printed circuit board having circuitry for electrically coupling said first and second sensor assemblies to said control module.

6. The system according to claim 1, wherein said optical sensor assemblies each comprise a plurality of optical emitters that are configured to emit light at different wavelengths to one another.

7. The system according to claim 6, wherein said detectors of said optical sensor assemblies are configured to be capable of detecting light from said plurality of emitters.

8. The system according to claim 3, wherein said elongate support is sized for insertion into a catheter that can be inserted into said lumen.

9. The system according to claim 1, wherein said probe can be decoupled from said control module for disposal.

10. The system according to claim 1, wherein said predetermined degree is chosen to be a degree in tissue vitality change that could be indicative of a potential failure of said anastomosis.

11. The system according to claim 10, wherein said control module is operable to alert an operator of said system if the indication of derived tissue vitality proximally of said anastomosis should vary by said predetermined degree from the indication of derived tissue vitality distally of said anastomosis.

12. The system according to claim 11, wherein said control module comprises a display and a display controller, said display controller being operable to control said display to display the indication of derived tissue vitality for the lumen distally of said anastomosis.

13. The system according to claim 12, wherein said display controller is operable to control said display to display the indication of derived tissue vitality for the lumen proximally of said anastomosis.

14. The system according to claim 13, wherein said display controller is operable to control said display to display an indication of tissue vitality difference between the indication of derived tissue vitality for the lumen proximally of said anastomosis and the indication of derived tissue vitality for the lumen distally of said anastomosis.

15. A system for monitoring anastomoses, the system comprising: a probe for insertion into a lumen of a subject and a control module for connection to said probe, wherein:
    the probe comprises first and second optical sensor assemblies, said first and second optical sensor assemblies each comprising an optical emitter operable to emit light and an optical detector for detecting light emitted by said optical emitter, said first and second sensor assemblies being spaced from one another so that following insertion of said probe into the lumen of said subject said first sensor assembly can be utilized to interrogate a first limb of an anastomosis and said second sensor assembly can be utilized to interrogate a second limb of said anastomosis,
    the control module is configured to be capable of operating said optical emitters of said first and second optical sensor assemblies to illuminate said first and second limbs of said anastomosis respectively, and to be capable of receiving signals from the optical detectors of said first and second optical sensor assemblies, signals from the optical detector of said first optical sensor assembly being representative of light reflected by tissue of said first limb of said anastomosis and signals from the optical detector of said second optical sensor assembly being representative of light reflected by tissue of said second limb of said anastomosis, said control module being further configured to compare the signals from the detectors of said first and second sensor assemblies with one another and derive therefrom an indication of tissue vitality in the first and second limbs of the lumen either side of said anastomosis, said indication of tissue vitality for both said first limb and said second limb is selected from one or more of tissue perfusion, blood flow, blood oxygenation, perfusion index (PI), incoming blood perfusion (PI), oxygen delivery (SpO2 and HbO2), oxygen consumption (HHb), and total blood volumes (tHb), and said control module is configured to alert an operator of said system if the indication of tissue vitality in said first limb of said anastomosis should vary by a predetermined degree from the indication of tissue vitality in said second limb of said anastomosis, said predetermined degree being chosen to be a degree in tissue vitality change that is indicative of a potential failure of said anastomosis.

16. A system for monitoring anastomoses, the system comprising a probe for interluminal insertion into a subject and a control module for connection to said probe, wherein:
    the probe comprises first and second optical sensor assemblies, said first and second optical sensor assemblies each comprising an optical emitter operable to emit light and an optical detector for detecting light emitted by said optical emitter, said first and second sensor assemblies being spaced from one another so that following insertion of said probe into a lumen of said subject said first sensor assembly can be utilised to interrogate a first limb of an anastomosis and said second sensor assembly can be utilised to interrogate a second limb of said anastomosis; and
    the control module is configured to be capable of operating said optical emitters of said first and second optical sensor assemblies for illumination of said first and second limbs of said anastomosis respectively, and to be capable of receiving signals from the optical detectors of said first and second optical sensor assemblies, signals from the optical detector of said first optical sensor assembly being representative of light reflected by tissue of said first limb of said anastomosis and signals from the optical detector of said second optical sensor assembly being representative of light reflected by tissue of said second limb of said anastomosis, said control module being further configured to: compare the signals from the detectors of said first and second sensor assemblies with one another and derive therefrom an indication of tissue vitality in the lumen either side of said anastomosis, and to determine if the indication of derived tissue vitality proximally of said anastomosis should vary by a predetermined degree from the indication of derived tissue vitality distally of said anastomosis.

* * * * *